Figure 1:
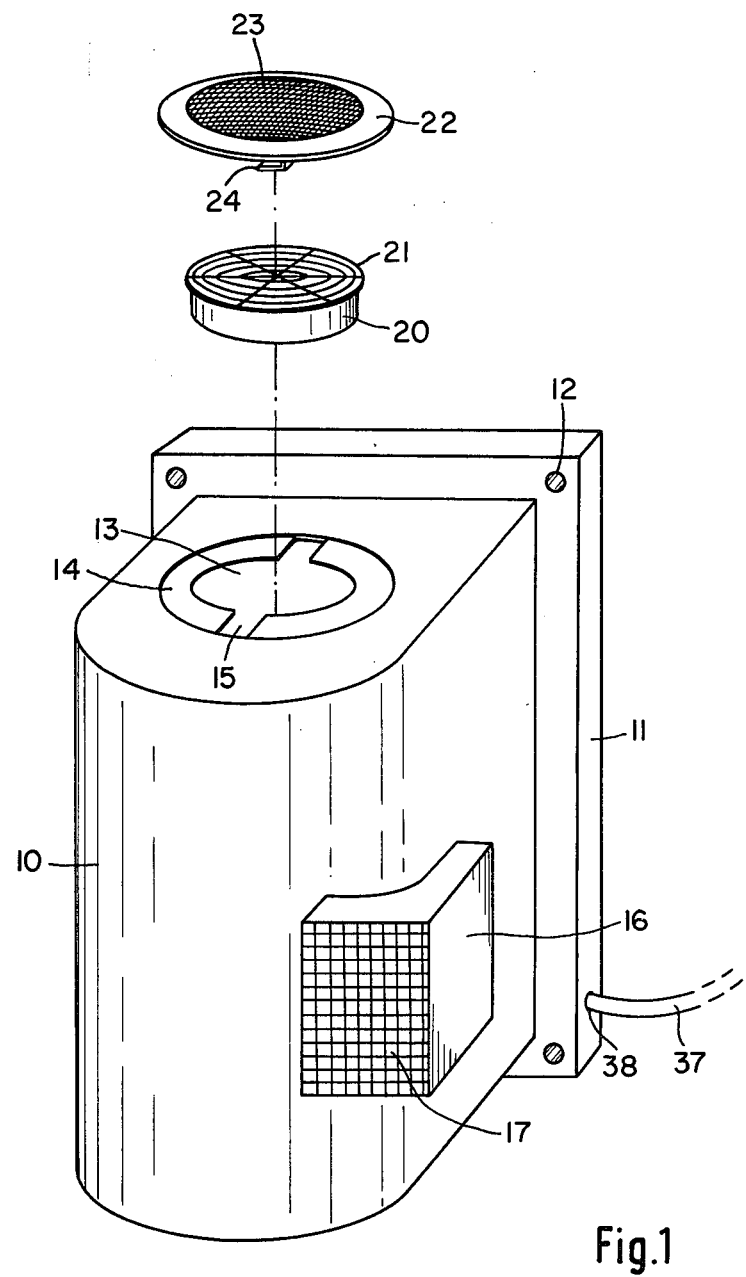

United States Patent [19]

Madjar

[11] 4,078,891
[45] Mar. 14, 1978

[54] AIR PURIFIER

[75] Inventor: Heinrich Madjar, Lb-Ossweil, Germany

[73] Assignee: Men-Sie Frischluftgerate-Vertriebe GmbH, Sachsenheim, Germany

[21] Appl. No.: 673,139

[22] Filed: Apr. 2, 1976

[51] Int. Cl.² .............................................. A61L 9/04
[52] U.S. Cl. ...................................... 21/74 R; 21/77; 21/126
[58] Field of Search ......................... 21/74 R, 126, 77

[56] References Cited

U.S. PATENT DOCUMENTS

| 1,238,068 | 8/1917 | Slater et al. | 21/74 R |
| 2,560,817 | 7/1951 | Pfeifer | 21/74 R X |
| 2,629,149 | 2/1953 | Yaffe | 21/74 R X |
| 3,055,066 | 9/1962 | Duncan | 21/74 R |
| 3,235,325 | 2/1966 | Storchheim | 21/74 R |
| 3,490,436 | 1/1970 | Hart | 21/74 R X |
| 3,633,881 | 1/1972 | Yurdin | 21/74 R X |
| 3,661,323 | 5/1972 | Farris | 21/74 R X |
| 3,744,216 | 7/1973 | Halloran | 21/74 R X |
| 3,990,848 | 11/1976 | Corris | 21/74 R X |

Primary Examiner—Morris O. Wolk
Assistant Examiner—Arnold Turk

[57] ABSTRACT

Air purifier in which a sealed housing having an air intake aperture and an air outlet aperture is provided with a blower mounted to circulate the air, and in which a filter and means for receiving a supply of disinfectant and/or perfume are arranged between the blower and the inlet aperture so as to be capable of replacement from the intake aperture. A presettable timer/switch is provided to control the supply of power to the blower, for intermittently actuating said blower.

3 Claims, 2 Drawing Figures

AIR PURIFIER

BACKGROUND OF INVENTION

The present invention relates to apparatus for purifying air and admixing disinfectants and/or perfumes therewith for rooms in which there is a concentration of injurious and/or odoriferous substances, in particular, lavatories.

It is precisely in such places as public lavatories that a powerful stench always prevails and is an annoyance to the user. The attempt has already been made to remedy this by suspending in such rooms ventilators (i.e.: air circulators) for perfume dispensers with solid odor compounds. These measures are, however, quite unsatisfactory, since the ventilators are as a rule not set in motion at the proper time, or not at all, and because the rate of volatilization of the solid perfumes is too slight to mask the stenches adequately.

It is an object of the present invention to provide apparatus of the aforementioned type in which ventilation (i.e.: air circulation) is used simultaneously with volatilizing disinfectants and/or perfumes, to purify the air.

It is a further object of the present invention to provide apparatus of the aforementioned type which is simple, low in cost and economically operable, in predetermined automatically initiated so as to provide a continual cleansing of the air.

These objects together with other objects and advantages will be obvious from the following disclosure.

SUMMARY OF THE INVENTION

According to the present invention, the apparatus for purifying air and for simultaneously admixing therewith disinfectants and/or perfumes comprises a sealed housing having an air intake aperture and an air outlet aperture, in which a blower is mounted to circulate the air. A filter and means for receiving a supply of disinfactant and/or perfume are arranged between the blower and the inlet so as to be capable of replacement from the intake aperture. A presettable time/switch controls the supply of power to the blower for intermittently actuating said blower.

Preferably, the blower is driven by an electric motor which can be switched periodically on and off by a time switch which is adjustable by means of a control element to thereby be initiated at different times and for different intervals.

With the foregoing apparatus the vitiated or bad air of the room is drawn into the house, purified by filtration, mixed with disinfectants and/or perfumes, and thereafter passed back to the room, as a fully purified, deodorized or perfumed air current.

Since all the parts of the apparatus are accommodated within a single housing, the apparatus can be made as a relatively small unit which may be inconspicuously and easily attached to one wall of the room. The components are few in number and are relatively simple thereby having a long and reliable operating life. The cost of the apparatus can be kept low in spite of the large number of functions, as the blower is used many times over and only the filter and disinfecting/perfume media need replacement from time to time. The time switch can be set in such a way that the working cycles of the apparatus can be adapted under optimum conditions to the particular use and frequency of use to which the room is made. The apparatus can be made to operate entirely automatically.

For this reason, provision is made for the filter as well as the disinfectant/perfume to be inserted interchangeably in the intake aperture of the housing.

The disinfectant/perfume insert used can be a tablet giving off volatile particles of the substances to be admixed with the air. It is also possible to use liquid perfumes, disinfectants or the like. The design may then be such that the liquid imparting the substances to be admixed with the air, is accommodated in a removable supply container provided with an absorbent wick, which may protrude at least partially from the supply container in the housing. In both cases, access to the insert and its interchangeability are furthered by the fact that the volatile media is arranged between the filter and the intake aperture of the blower and is interchangeable via the intake aperture of the housing when the filter is removed. So that the circulation of the air drawn in between the intake aperture and the outlet aperture is not impaired, a perforated supporting plate is arranged between the blower and filter on which the container holding the media can be removably secured.

The time switch, on the other hand, is fastened to a conductor plate arranged below the blower, so that the air duct between the intake and the outlet is not interfered with. The conductor plate is formed of insulating material on which a printed electrical circuit is located, so as to permit easy removal and replacement of parts.

The filter serves to remove particulate matter from the foul air so that a more effective areosol mixture is obtained and so that the blower can remain clean over a long period of time.

Full details of the present invention are set forth in the following description and illustrated in the accompanying drawings.

BRIEF DESCRIPTION OF THE DRAWINGS

In the drawings:

FIG. 1 is a perspective partially exploded view of the apparatus showing the interchangeable filter and cover lid; and FIG. 2 is a rear elevational view showing the components of the apparatus.

DESCRIPTION OF THE INVENTION

As seen in FIG. 1 the apparatus is embodied in a generally hollow housing comprising a unitary dome or tunnel like body 10 having a lateral edge 11 extending completely about its periphery. The edge 11 is provided with holes 12 which permit the same to be mounted on a wall or other support by use of conventional screw means. At the upper end of the body 10 there is provided an intake aperture or opening 13 which is formed with a inwardly directed edge 14, recessed or stepped below the plane of the end portion of the body and which is provided with radially directed slots 15 so as to provide one half of a cooperating bayonet type locking means which will be more fully described later.

On the curved frontal wall of the body 10, an outlet aperture is formed comprising a tangentially directed duct 16 covered by a screen like grating 17. Preferably, the housing is formed of a unitary plastic molding so as to be sealed tightly except at the intake and outlet. Metal integrally formed housings may also be used, if desired.

As seen in FIG. 2 the rear of the peripheral bordering edge 11 is provided with a flange 18 running completely around its periphery forming a frame for the receipt of a backing plate, not shown, which is attached by suitable screw means received in threaded recesses 19 integrally formed in the border 11. Suitable seal means such as rubber or plastic foam gasket strips are placed along the edge of the housing, between the rear of the bordering edge 11 and the not shown backing plate, so as to seal the interior of the housing completely. The backing plate may, however, be removed for insertion and replacement of the component parts of the apparatus.

An air filter canister 20 having a peripheral flange 21 is seated within the intake aperture 13, so that the flange 21 rests upon the stepped edge 14. The filter may be in the form of multiple screens, a porous mass of steel wool, or a mass of fibrous material. Porous paper sheets or the like may also be used. The diameter of the flange 21 is less than that of the aperture 13 but greater than the edge 14 so that it can rest thereon. Placed over the filter is a lid comprises an annular ring 22 having a diameter greater than the aperture and which is provided with a mesh-like screen 23. The underside of the ring 22 is provided with resilient like L-shaped brackets 24 which fit first within the slots 15 so that, when the ring 22 is rotated, it forms the cooperating second half portion of the bayonnet type closing member. In this manner, the ring 22 removably seats the air filter canister 20 firmly within the aperture 13. Air drawn through the screen 23 will thus pass through the filter canister 20 into the housing.

Figure 2:
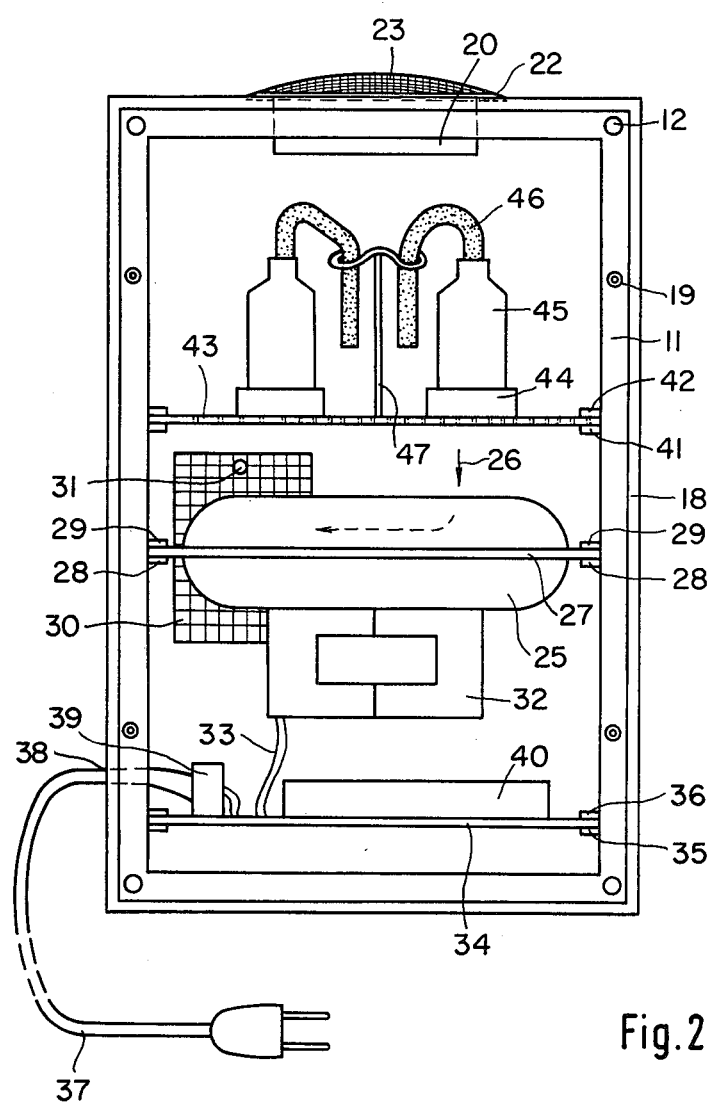

Turning to FIG. 2, the interior of the housing contains a centrifugal fan or air blower 25 having an axial intake 26 and a tangential outlet leading into the duct 16 (FIG. 1). The blower 25 is housed in a disc-like body having a peripheral edge 27 which slidably fits in and is secured by a pair of molding strips 28 and 29 unitarily or integrally formed on the inner wall of the housing body 10. In this manner, the blower 25 may be removably inserted within the body. In addition, the blower is provided with a supporting screen 30 or wall at its outlet end, which may be additionally secured by screw means 31 to the interior surface of the housing body 10 so as to maintain the outlet in fixed alignment with the duct 16. Other suitable supporting brackets may be used.

The blower 25 is driven by an electric motor 32 mounted on the blower housing and depending, as seen in FIG. 2, below the outlet opening so as not to interfere with the air flow. Electrical leads 33 extend from the motor 32 to a conductor plate 34 on which is formed by conventional means a printed electrical circuit, which is held in a similar manner as the blower, in a pair of molding strips 35 and 36 unitarily or integrally formed with the interior of the housing. The printed circuit on the conductor plate 34 is connected to a source of electrical current, such as usual household current, by a lead 37, which extends through a hole 38 formed in the peripheral bordering edge 11 of the housing. The interior ends of the lead 37 are held or encapsulated in a conventional stress relieving fixture 39, such as a plastic block, so as to prevent disengagement of the connection between it and the connecting plate 34, and to prevent short-circuiting.

Mounted on the conductor plate 34 in contact with the printed circuit, is an adjustable time and switch mechanism 40. The timer and switch mechanism is of conventional electrical or electronic construction and is capable of being pre-set and adjusted, so that it controls the activation of the motor 32 as to the time of activation, and the interval during which such activation extends. The motor 32 is connected to the timer/switch via the leads 33.

Mounted above the blower 25, in a pair of molding strips 41 and 42, is an open-weave lattice-like plate 43 upon which is secured a pair of holders 44, each adapted to removably receive and securely hold a bottle-like container 45, adapted to hold a disinfectant and/or perfume media. The holders 44 may be provided with spring-like or plastic resilient members, to further secure the bottles 45. Extending from each of the bottles 45, is an absorbent wick 46, the ends of which are held in a wire-like bracket 47, secured to the mounting plate 43. The bottle-like containers 45 are of course adapted to hold a liquid media. However, the liquid media may be replaced by solid, highly volatile media in which case the use of absorbent wicks may be dispensed with. In addition, volatilizing tablets may be located in the holders 44.

It will be observed, that the removable retaining ring 22, securing the filter 20 within the intake aperture 13 permits the easy removal and replacement of not only the filter, but also of the containers and/or media for the disinfectant and/or perfume. The opening 13 should therefore be made sufficiently large, to permit the manual removal of the filter and of the containers holding the media. The enlarged opening further permits a sufficient degree of air flow through the housing. The lattice-like mounting 43 further does not inhibit the air flow. The apparatus may be completely assembled and enclosed by the not shown backing plate and stored and shipped in this condition, without the disinfectant and/or perfume media which may be later inserted, after the apparatus is attached to the wall or support in the room to be treated. If desired, the media may be installed during assembly in sealed or capped containers which are merely opened upon installation of the apparatus.

The timing device 40 may be pre-set at assembly or may be adjusted at installation to provide the desired timing sequence.

In any event, it will be seen, that when the blower 25 is operated, air will be drawn through the screen 23 purified, i.e. removed of particulate matter, by passing through the filter 20, and thereafter come in contact with the moistened wicks 46. On contact with the wicks 46, the air becomes enriched and becomes admixed with the disinfectant and/or perfume media, thereafter passing through the lattice-like mounting plate 43 into the intake 26 of the blower 25. The thus purified and enriched air is passed immediately to the outlet duct 16, to be discharged into the room, being treated. By pre-setting the timer mechanism 40, the blower can be made to operate in such a sequence, depending upon the nature and extent to which the room being treated is actually put in use, so that an automatic cleansing of the air within the room is effected in a manner to maintain the room constantly at a proper level of cleanliness and desirable odor.

Various modifications and changes have been discussed herein, others will be obvious to those skilled in the art. For example, when a solid disinfectant and/or perfume media is employed, the directional disposition of the housing can be modified. In addition, the exact form of the housing can also be varied from its dome or tunnel like configuration to a more rectangular shape. Accordingly, it is intended that the present disclosure be taken as illustrative only, and not as limiting the scope of the invention.

What is claimed:

1. Apparatus for admixing with air a volatile media such as a disinfectant or perfume, comprising a hollow housing formed by a unitary tunnel-like body having an open side, end walls and an outward edge extending about the periphery of said open side, for securement to a wall or support said tunnel-like body defining a duct-like air path, an intake opening formed in one of the end walls of said housing, a filter removably mounted in said intake opening, a blower mounted in said housing spaced from said intake opening for drawing air into the interior of said housing, said blower comprising a centrifugal fan having a disc-like housing, an axial inlet and a tangential outlet, said blower being mounted on a solid horizontal plate dividing said housing with said plate being mounted for removal through the open side of said tunnel-like body, an outlet opening formed in the tunnel-like body of said housing in communication with the tangential outlet of said blower for expelling air therefrom, a volatile media, a perforated plate for support of said volatile media removably mounted in said tunnel-like body between said air inlet and said blower and in proximity to said intake opening, an electric motor for driving said blower mounted beneath said blower in said tunnel-like body, and means for controlling the operation of said blower including a timer switch connected to said motor, said time switch being adjustable to activate said motor at predetermined selected times and for predetermined selected duration to periodically draw air into said housing and to cause said air to admix with said volatile media within said housing, said admixed air and volatile media thereafter flowing outwardly of said outlet opening and including a printed circuit conductor plate removably mounted in said housing below said blower with at least said control means for said blower being mounted on said conductor plate.

2. The apparatus according to claim 1 wherein said volatile media is a highly volatile solid.

3. The apparatus according to claim 1 wherein said volatile media is a liquid, said liquid being contained in a container having a wick extendable at least partially into the air path.

* * * * *